United States Patent [19]
Pruss et al.

[11] Patent Number: 5,643,596
[45] Date of Patent: Jul. 1, 1997

[54] HEMOSTATIC PATCH

[75] Inventors: Thaddeus P. Pruss, Baltimore, Md.; James A. Will, Columbus, Wis.

[73] Assignee: Clarion Pharmaceuticals, Inc., Madison, Wis.

[21] Appl. No.: 474,127

[22] Filed: Jun. 7, 1995

Related U.S. Application Data

[63] Continuation of Ser. No. 146,360, Nov. 3, 1993, abandoned.

[51] Int. Cl.$^6$ ..................................... A61K 9/70
[52] U.S. Cl. .............. 424/426; 424/422; 424/423; 424/443; 424/444; 424/484; 424/499; 514/2; 514/21; 514/557; 514/561
[58] Field of Search ................. 424/426, 422, 424/423, 443, 444, 484, 499; 514/2, 21, 557, 561

[56] References Cited

U.S. PATENT DOCUMENTS

| | | | |
|---|---|---|---|
| 2,610,625 | 9/1952 | Sifferd et al. | 128/156 |
| 3,157,524 | 11/1964 | Artandi | 106/122 |
| 3,731,683 | 5/1973 | Zaffaroni | 128/268 |
| 3,797,494 | 3/1974 | Zaffaroni | 128/268 |
| 3,854,480 | 12/1974 | Zaffaroni | 128/260 |
| 3,908,018 | 9/1975 | Choay | 424/319 |

(List continued on next page.)

FOREIGN PATENT DOCUMENTS

| | | |
|---|---|---|
| 0 059 265 | 9/1982 | European Pat. Off. . |
| 0090997 | 10/1983 | European Pat. Off. . |
| 1960614 | 6/1976 | Germany . |
| 292840 A5 | 8/1991 | Germany . |
| 54-98091 | 8/1979 | Japan . |
| 1099565 | 4/1989 | Japan . |

(List continued on next page.)

OTHER PUBLICATIONS

"The Effectiveness of a Fibrinogen–Thrombin–Collagen–based Hemostatic . . . ", Schelling et al., *Annals of Surgery*, vol. 205(4), Apr. 1987, pp. 432–435.

"Autologous Fibrin Tissue Adhesive Biodegration and Systemic Effects", Abstracts, Harris et al., *Laryngoscope*, vol. 97(10), Oct. 1987, pp. 1141–1144.

"Application of Fibrinogen–Thrombin–Collagen–Based Hemostatic Agent . . . ", Schelling et al., *T. Journal of Trauma*, vol. 28(4), Apr. 1988, pp. 472–475.

"Fibrin Glue: A Review of the Preparation, Efficacy, and Adverse . . . ", Abstract, Thompson et al., Drug Intell. Clin. Pharm., vol. 22(12), Dec. 1988, pp. 946–952.

"Pepsin Fibrinolysis of Artifical Clots . . . the Effect of pH and . . . ", Abstract, *Surg. Endosc.*, vol. 3(3), 1988, pp. 148–151.

"Autologous Fibrin Glue in Full–Thickness Skin Grafting", Abstract, Chakravorty et al., Ann. Plast. Surg., vol. 23(6), Dec. 1989, pp. 488–491.

(List continued on next page.)

*Primary Examiner*—Gollamudi S. Kishore
*Attorney, Agent, or Firm*—Millen, White, Zelano, & Branigan, P.C.

[57] ABSTRACT

A fibrogen-free substrate having as a hemostatic agent on a surface thereof a mixture of a clot-promoting amount of thrombin and an amount of epsilon aminocaproic acid (EACA) effective to accelerate the rate of blood clotting induced by the thrombin is useful as a hemostatic patch which is safe, inexpensive and which rapidly controls bleeding from a wound. A patch which rapidly stanches the flow of blood from a lesion on a parenchymal organ by pressing it against the surface of the organ for 3–5 minutes, is produced by applying thrombin, EACA and $CaCl_2$ to a rigid sheet of biodegradable foam, such as an absorbable gelatin sponge, and compressing the dry sheet to produce a flexible sheet which conforms to the contour of the organ without the necessity of pre-moistening. The problem associated with thrombin-fibrinogen glues of adhesion of the wounded surface of the organ to adjacent tissue is avoided by applying the hemostatic agent to only the wound-contacting face of the sheet.

17 Claims, 4 Drawing Sheets

OTHER PUBLICATIONS

"Fibrin Glue: The Perfect Operative Sealant?", Gibble et al., *Transfusion*, vol. 30(8), 1990, pp. 741–747.

"Antifibrinolytic Activities of alpha–N–actyl–L–lysine . . . ", Abstract, Anonick et al., *Arrerioscler Thromb.*, vol. 12(6), Jun. 1992, pp. 708–716.

"Haemostatic Activity of Ethamsylate and Aminocaproic Acid . . . ", Abstract, Horak et al., *Biomaterials*, vol. 13(8), 1992, pp. 521–526.

"Haemostyptic Preparations on the Basis of Collagen Alone . . . ", Schiele et al., *Clinical Materials*, vol. 9, 1992, pp. 169–177.

"Biotech Gets a Grip on Cell Adhesion", Travis, *Science*, vol. 260, May 1993, pp. 906–908.

"Amicar", Physician's Desk Ref., pp. 1194–1195.

"Gelfoam", Physician's Desk Ref., pp. 2338–2340.

"Hemopad", Physician's Desk Ref., pp. 627–628.

"Surgicel and Surgical Nu–Knit", Physician's Desk Ref., pp. 1151–1153.

"Topical USP Thrombogen", Physician's Desk Ref., pp. 1153–1154.

"Thrombostat", Physician's Desk Ref., pp. 1765–1766.

"KALTOSTAT Wound Dressing", Ad. (2 pp.), Calgon Vestal Labs.

"HELISTAT, Absorbable Collagen Hemostatic Sponge", Ad. (4 pp.), Calgon.

U.S. PATENT DOCUMENTS

| Number | Date | Inventor | Class |
|---|---|---|---|
| 4,006,220 | 2/1977 | Gottlieb | 424/101 |
| 4,167,945 | 9/1979 | Gottieb | 128/334 |
| 4,191,751 | 3/1980 | Gottlieb | 424/177 |
| 4,265,233 | 5/1981 | Sugitachi et al. | 128/156 |
| 4,362,567 | 12/1982 | Schwarz et al. | 106/157 |
| 4,363,319 | 12/1982 | Altshuler | 128/156 |
| 4,390,519 | 6/1983 | Sawyer | 424/28 |
| 4,414,976 | 11/1983 | Schwarz et al. | 128/334 |
| 4,427,650 | 1/1984 | Stroetmann | 424/46 |
| 4,427,651 | 1/1984 | Stroetmann | 424/46 |
| 4,453,939 | 6/1984 | Zimmerman et al. | 604/368 |
| 4,515,637 | 5/1985 | Cloca | 424/94 |
| 4,600,574 | 7/1986 | Lindner et al. | 424/28 |
| 4,606,337 | 8/1986 | Zimmerman et al. | 128/156 |
| 4,627,879 | 12/1986 | Rose | 106/124 |
| 4,637,815 | 1/1987 | Lemole | 604/28 |
| 4,642,118 | 2/1987 | Kuroyanagi et al. | 623/15 |
| 4,650,678 | 3/1987 | Fuhge et al. | 424/101 |
| 4,683,142 | 7/1987 | Zimmerman et al. | 427/2 |
| 4,738,849 | 4/1988 | Sawyer | 424/449 |
| 4,743,337 | 5/1988 | Freeman | 128/156 |
| 4,891,359 | 1/1990 | Saferstein et al. | 514/21 |
| 4,957,902 | 9/1990 | Grinnell | 514/17 |
| 5,057,414 | 10/1991 | Stief et al. | 435/13 |
| 5,100,429 | 3/1992 | Sinofsky et al. | 606/195 |
| 5,201,745 | 4/1993 | Tayot et al. | 606/151 |
| 5,266,327 | 11/1993 | Agrez | 424/426 |
| 5,290,552 | 3/1994 | Sierra et al. | 424/94.64 |
| 5,330,974 | 7/1994 | Pines | 514/21 |

FOREIGN PATENT DOCUMENTS

| | | |
|---|---|---|
| 700129 | 11/1979 | U.S.S.R. |
| 908357 | 2/1982 | U.S.S.R. |
| 921540 | 4/1982 | U.S.S.R. |
| 90/13320 | 11/1990 | WIPO |
| WOA9306855 | 4/1993 | WIPO |

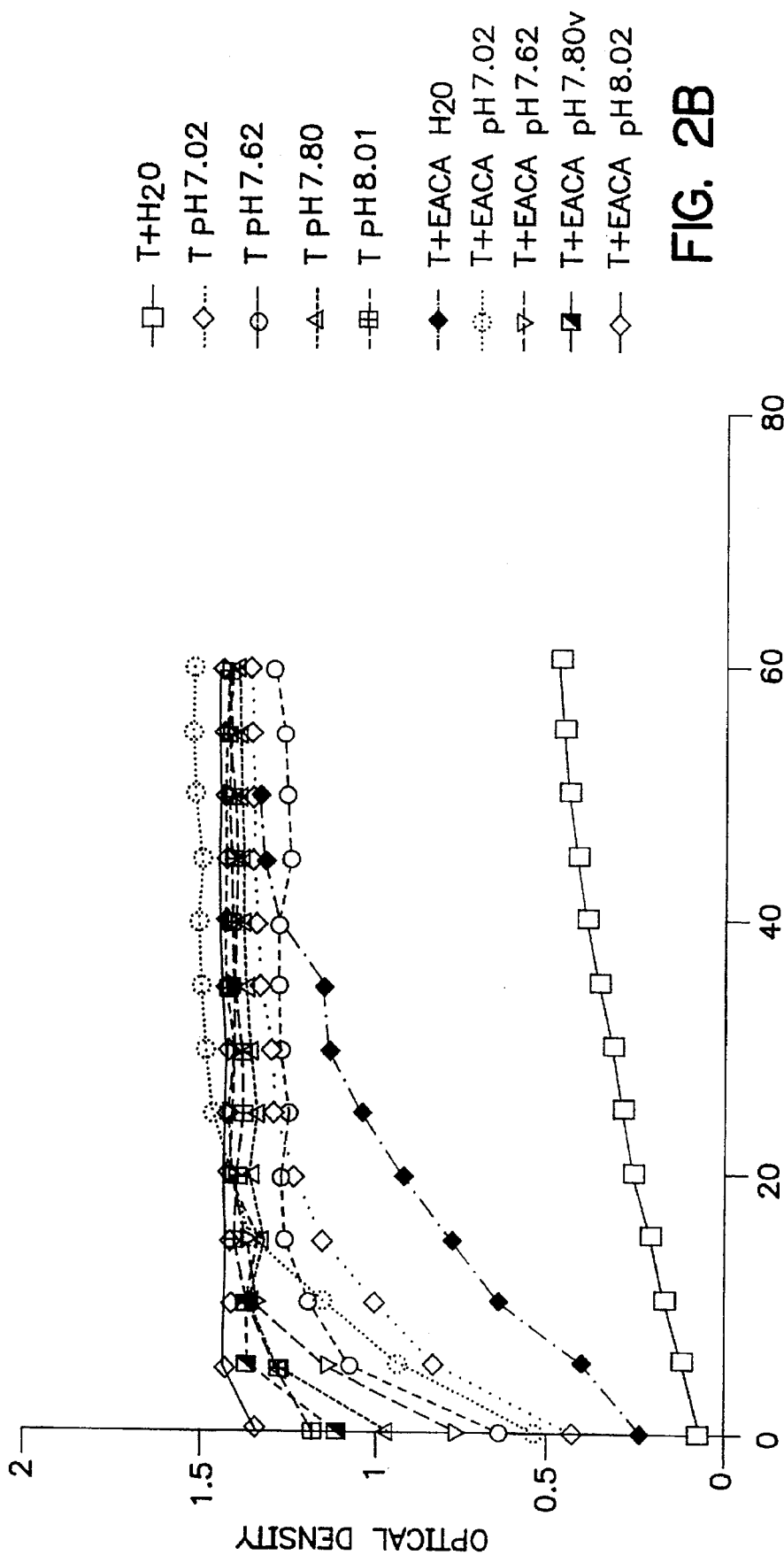

HEMOSTATIC PATCH

This application is a continuation of application Ser. No. 08/146,360, filed Nov. 3, 1993, now abandoned.

BACKGROUND OF THE INVENTION

A hemorrhage of a blood vessel, body tissue, organ or bone can result in blood loss leading to hypovolemic shock and death. In hemophiliacs and patients receiving anticoagulant medication, such as often prescribed postoperatively for heart surgery, the problem of rapid blood loss is even more acute.

Attempts have been made to devise a fast, effective and inexpensive method for curbing blood loss, including pastes containing coagulation-enhancing factors. One such coagulation enhancing substance employed to assist a cessation of bleeding or "hemostasis" is human fibrinogen, most commonly employed as a "fibrin glue".

Fibrin glue is composed of a mixture of human fibrinogen and bovine thrombin. It is sold as a kit containing separate vials of fibrinogen and thrombin solutions. These solutions are mixed together and applied to the wound in various ways, including as a paste, as a spray or on a patch.

Fibrin glue, however, is an inconsistent and ineffective therapy for hemostasis. The mixing, soaking, and coating of a patch with fibrin glue requires time-consuming and cumbersome procedures. Each of the preparation steps introduces potential errors and thus their efficacy varies with the experience of operating room personnel. Moreover, during the preparation of such solution, further hemorrhage occurs and the solutions are washed away by intense bleeding. Despite the headway made in fibrinogen compositions and surgical techniques, these pitfalls in achieving hemostasis underscore the need for development of a suitable product.

An improvement over fibrin glue, marketed in Europe consists of a biodegradable collagen patch onto which is impregnated bovine thrombin, aprotinin and human fibrinogen (the "TAF" patch). An example of a TAF patch is the TachoComb® patch marketed in Europe by Hafslund Nycomed Pharma, Del. The patch also contains calcium chloride to enhance coagulation. In use, this patch is removed from its package, dipped into saline solution and applied to the bleeding organ with light pressure for at least five minutes. When the bleeding has stopped, the patch is left in place by the surgeon and the cavity closed.

A major drawback to the use of fibrin glue and the TAF patch is that both contain human fibrinogen, a protein purified from human blood. Because of the high risk of HIV and hepatitis viral contamination, the Food and Drug Administration revoked the use of human fibrinogen in the United States in 1978. In addition to the safety concerns, human fibrinogen purified from human plasma is very expensive.

A TAF patch also requires refrigeration in order to stabilize the coagulation-enhancing agents contained in the patch. This requirement prohibits certain field applications of the patch, where refrigeration facilities are unavailable. Another problem with a TAF patch that surgeons cite is its inflexibility, that is, the patch does not conform easily to the shape of the body surface to which it is applied.

A hemorrhage of a parenchymal organ, such as the spleen, liver, lung or pancreas, which can result from trauma or surgery, is particularly difficult to treat. Parenchymal organs are difficult to ligate because the tissue is easily torn, pulverized or crumbled. As a result, surgeons often resort to the use of electrocautery, which can lead to further destruction of the patient's tissues.

Thus, an effective hemostatic patch is desired which is safe from deadly viral contamination and even stops bleeding in the problematic hemorrhages of parenchymal organs. A patch is further desired that is inexpensive, easy to use and that molds easily to body contours. Also a need exists for a patch that withstands elevated temperatures without requiring refrigeration and retains hemostatic efficacy.

SUMMARY OF THE INVENTION

According to the present invention, an effective hemostatic patch is produced comprising a matrix and at least one hemostatic agent, epsilon aminocaproic acid. The patch does not require as an ingredient any exogenous human protein, such as fibrinogen, which thereby avoids introduction of unsafe contaminating viruses. The present hemostatic patch is inexpensive, easy to use, thermally stable, and antibacterial, as well.

BRIEF DESCRIPTION OF THE DRAWINGS

FIG. 2 demonstrates the effects of pH on thrombin activation at 37° C.

DETAILED DESCRIPTION OF THE PREFERRED EMBODIMENTS

Figure 1:
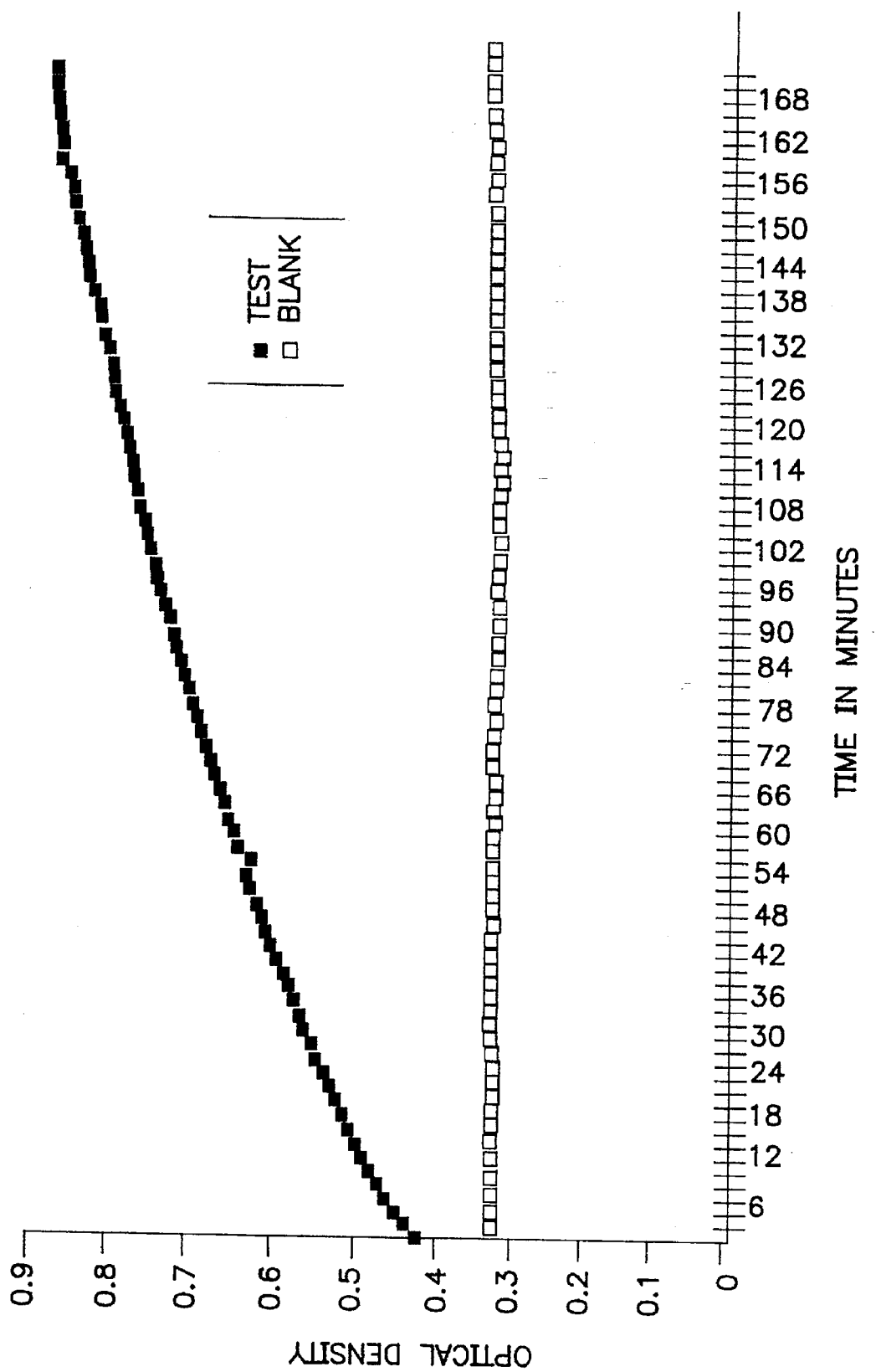
FIG. 1 displays a control experiment showing the thrombin activation at 37° C. and physiological pH.

According to the present invention, a hemostatic patch is provided that comprises a shaped structural element that is a biodegradable matrix, such as absorbable gelatin sponge or calcium alginate, to which is applied a hemostatic agent that contains epsilon aminocaproic acid, "EACA." EACA is an inhibitor of clot degradation. In the body, clot formation and clot breakdown are competing processes. EACA inhibits the production of plasmin, an enzyme that degrades clots. Plasmin degrades clots by solubilizing fibrin, an important component of clots, in a process called fibrinolysis. By inhibiting the formation of plasmin which breaks down clots, EACA inhibits fibrinolysis and drives the reaction conditions at the patch/biological interface in favor of clot formation. A hemostatic patch according to the invention thus comprises an amount of EACA effective for inhibiting fibrinolysis.

Surprisingly, it has been discovered that EACA functions as a hemostatic agent in a patch in a manner that approximates the effectiveness of fibrinogen, a coagulation factor that, in solution, converts to fibrin in the presence of thrombin. Fibrinogen is an active ingredient found in other hemostatic patches. EACA, however, is devoid of the hazards that accompany use of fibrinogen.

Moreover, according to the present invention, it has been determined, surprisingly that EACA in the matrix of a patch provides an alkaline environment that accelerates the activation of thrombin. In comparison with thrombin activation measured in the absence of EACA (FIG. 1, closed boxes), EACA greatly increases thrombin's activity (FIG. 2). This phenomenon holds true whether the EACA acts on thrombin present in the blood endogenously or on thrombin that is supplied externally in a patch. Thus, it has been discovered that a patch comprising EACA exerts a dual hemostatic action by (1) slowing clot degradation by inhibiting plasmin formation and (2) accelerating clot formation by activating thrombin.

Therefore, a method is provided for accelerating the activity of thrombin by increasing the pH of the local environment of a patch according to the invention. Such a patch comprises a matrix and a "thrombin enhancing compound" capable of raising the pH in a solution in the local environment of the patch sufficient to increase the activation of thrombin. Such a compound is capable of raising the pH of the local environment to a pH in the range of 7.0–9.0 inclusive, more advantageously between pH 7.02–8.02 inclusively, and even further advantageously, between pH 7.62–8.02, inclusively.

According to the present invention, an alkaline solution is created in the local environment of the patch as the thrombin enhancing compound solubilizes upon its contact with blood. Then, thrombin present in the blood and, optionally, thrombin provided as an exogenous ingredient of the patch mixes with the alkaline solution in the local environment of a patch and thereby is activated.

Advantageously, the thrombin-enhancing compound provided in the patch for increasing pH is EACA. A "sterile buffer" which is pharmaceutically acceptable and capable of buffering the local pH in the patch to alkaline conditions, (i.e., between a pH of 7.0–9.0, more advantageously pH 7.02–8.02, and even further advantageously, 7.62–8.02), is suitable as a thrombin-enhancing compound, as well. For example, Tris buffer is an effective thrombin-enhancing sterile buffer, as shown in FIG. 2, open diamond-shaped graphical plot. Other sterile buffers that buffer the pH in this range are contemplated, such as Hepes buffer, for example. Accordingly, in a more advantageous patch, EACA and Tris (or other) buffer both are provided in the matrix of the patch.

Yet another surprising advantage of EACA has been discovered. EACA possesses antibacterial properties. According to the present invention, it has been demonstrated that EACA exerts dose-dependent inhibition of both *S. aureus* and *E. coli* growth (FIGS. 3A, 3B and 4A, 4B, respectively). Therefore, the EACA/matrix patch according to the present invention is very desirable for its antibacterial effects on microorganisms present at the wound site where a patch is applied.

Another advantage of EACA is that it contains no foreign peptides of animal origin. For example, a non-human fibrinogen hemostatic agent in some humans will trigger an immune response or allergic-like reaction.

Thus, a patch according to the invention can contain as a sole hemostatic agent EACA dispersed within a matrix or applied to a surface of a matrix in an amount effective for inhibiting fibrinolysis and thereby stimulating clot formation. A biodegradable "matrix" as referred to herein, and as employed in any of the present embodiments of the invention, is selected from, but not limited to, the group consisting of absorbable gelatin sponge, calcium alginate, calcium/sodium alginate, collagen, and oxidized regenerated cellulose. A matrix of other forms of collagen, such as crosslinked collagen, esterified collagen or chemically modified collagen as taught by U.S. Pat. No. 4,390,519 to Sawyer, and other conventional matrices utilized in hemostatic patches, are contemplated for use with EACA according to the present invention. Four matrices that are advantageous for use with EACA include absorbable gelatin sponge, calcium alginate, calcium/sodium alginate, and collagen.

A first embodiment of the invention therefore provides a patch comprising a matrix of absorbable gelatin sponge "G" and a hemostatic agent, EACA "E." This embodiment, "GE", preferably also can contain calcium, "G(Ca++)E." Advantageously, the GE or G(Ca++)E patch need not contain or fibrinogen to function effectively to control hemorrhage of a parenchymal organ. As a result, both GE and G(Ca++)E, have good thermal stability and can be stored for months to a few years without refrigeration and losing effectiveness. The GE and G(Ca++)E patches are useful for field and emergency use, since each may be stored in a ready-to-use state for a lengthy period, even in absence of refrigeration. Both also are much less expensive to make than patches which contain fibrinogen.

The many representative embodiments of the present invention are referred to herein most easily by acronyms, e.g., GE. These acronyms are indicative of the individual components (Table 1) found in the patches created in accordance with the invention.

TABLE 1

PATCH COMPONENT CODES:

G = gelatin foam patch alone, e.g., Gelfoam ®
CA = calcium alginate
CVA = calcium/sodium alginate, e.g., Kaltostat ®
C or CVC = collagen or collagen(Helistat ®), respectively
E = EACA
(Ca++) = calcium
T = thrombin
R = RGD peptide
P = protamine sulfate
F = Fibrinogen
(f) = freshly applied compound (Example 7)
GT(Ca++)E = "Hemarrest ™" patch In other embodiments, a GE or G(Ca++)E patch further comprises an effective amount of thrombin for stimulating hemostasis and thus is designated as "GTE" or "GT(Ca++)E." A thrombin molecule is most stable at temperatures between 2°–8° C. However, these patches can be stored for a limited period of time at room temperature. In fact, because addition of thrombin enhances the GE and G(Ca++)E patches' effectiveness, these patches are very useful outside the clinic for field use, such as for emergency or military purposes.

Although it is understood that exposure to extreme environmental conditions may render thrombin present in the patch partially or totally inactive, the activity of the remaining GE or G(Ca++)E patch would not be substantially affected.

In the GE and GE(Ca++) patches, and all patches described herein that employ an absorbable gelatin sponge$^{USP}$ as a matrix, the matrix is advantageously a flat layer of gelatin foam, more advantageously, Gelfoam®, and even more advantageously, compressed gelatin foam or compressed GelFoam®. The effectiveness of patches of the present invention in promoting clot formation is enhanced by the lattice structure of the gelatin foam, which promotes enzyme substrate interactions. In particular, the gelatin foam structure enhances contact between thrombin provided exogenously in the patch with endogenous fibrinogen present in the blood exuding from the wound.

Additional hemostatic agents can be applied to the GE patch in amounts effective for stimulating hemostasis, including, but not limited to: thrombin "T", an enzyme which converts fibrinogen to fibrin; calcium, sodium, magnesium or other ions that stimulate hemostasis; and optionally, fibrinogen, "F".

In terms of ion additives, calcium chloride is generally a preferred additive for introducing a calcium ion into the patch.

"EACA analogs," or compounds that possess a similar hemostatic activity and a chemical structure to that of EACA, can be used instead of, or in addition to, EACA in a patch according to the invention. Possible EACA analogs contemplated for addition to a matrix include EACA derivatives having bioisosteric functional groups. EACA's carboxylic acid group can be substituted, for example, by sulfonic or sulfinic acid ($-SO_2H$ and $-SO_3H$) or phosphonic acid groups. Examples of analogs include, but are not limited, to 5-aminopentanoic a acid, 7-aminoheptanoic acid, 8-aminooctanoic acid, provided that these compounds exert a hemostatic activity.

The molecules "thrombin" and "fibrinogen" as defined herein are meant to include natural thrombin and fibrinogen molecules derived from an animal or human origin, a synthetic form or a recombinant form of the molecules, including functionally active analogs that effectively maintain the enzyme's clot promoting activity in an animal or human. The species of animal from which the molecule is derived can vary and depends on the intended use of the patch. For example, a patch intended for human use for safety reasons contains non-human thrombin and preferred in this context is bovine thrombin. By avoiding use of human fibrinogen, risks associated with viral contamination of purified blood products (particularly with fibrinogen) are minimized. Indeed, the ingredients EACA, thrombin and GelFoam® all are approved by the U.S. Food and Drug Administration for human use.

In yet another embodiment, a patch is provided having a matrix composed of calcium-sodium alginate "CVA" or calcium alginate "CA," and a hemostatic layer of EACA "E." It is understood that calcium alginate can be substituted for calcium/sodium alginate in the discussion and examples hereafter, without substantial differences in results.

The embodiment, "CVAE", advantageously contains calcium ion and thrombin as well. It also is less expensive as compared with a patch that contains fibrinogen. Similar to the GE patch, the CAE patch can include additional hemostatic agents including, but not limited to, thrombin, calcium or sodium or other ions in amounts that are effective to stimulate or accelerate hemostasis. These patches further can contain additives as described herein, as well.

In another embodiment, an effective amount of the active peptide, RGD, "R" or RGDS effective to stimulate wound healing is added to a patch comprising GE or CAE, and thus such a patch is designated as GER or CAER. The tripeptide RGD is composed of arginine, glycine and aspartic acid, and optionally serine "RGDS," and is the active site of fibrinogen and fibronectin. RGD accelerates wound healing and is believed to stimulate fibroblast migration.

The RGD additive is also much less expensive than fibrinogen. RGD can be synthesized easily using conventional solid phase chemistry at a fraction of the cost of obtaining fibrinogen, which currently must be obtained by purification from a natural source.

In yet another embodiment, an amount of the agent protamine sulfate "P" effective to neutralize heparin present in the local environment of the patch is added to any of the aforementioned patches comprising EACA and a matrix. Protamine sulfate neutralizes heparin or vitamin K antagonists that are present in the blood of certain patients or animals being treated with a hemostatic patch. A patch comprising GEP or CAEP, for example, is prescribed for persons undergoing parenteral therapy with heparin. In particular, a patch that further contains thrombin would be effective in patients taking dicumarol. A patch containing protamine sulfate is preferably stored at refrigerated temperatures of 2–8 degrees Celsius to maintain the activity of protamine sulfate.

An additional advantage of the patches according to the present invention is that the matrices, such as absorbable gelatin sponge or calcium alginate, and the hemostatic agents, especially EACA and thrombin, and the additive, RGD, all are relatively inexpensive. It is estimated that production of a "standard-size" rectangular patch of about 9.5×4.8 cm, having a thickness of about 2.5 mm would cost substantially less than a TAF patch of the same size.

Patches according to the present invention exhibited efficacy in inducing hemostasis in freely bleeding lesions of the spleen, liver and kidney of an anesthetized pig. Surgical lesions induced in parenchymal organs of pigs provide a good model system for hemostasis in the analogous human organs as evidenced by preclinical studies performed on pigs and dogs for the TachoComb® patch. Schiele et al., *Clinical Materials* 9:169 at page 172 (1992). See also, *SWINE AS MODELS IN BIOMEDICAL RESEARCH*, Swindle, M., Iowa State Univ. Press (1992). Indeed, surprisingly, patches according to the present invention performed better than TachoComb® in the liver, while in the kidneys, the patch containing a matrix of GelFoam®, thrombin and 100 $mg/cm^2$ EACA performed equally as well as the TachoComb® patch. The results of that comparative experiment are presented in Example 3 herein.

Another important advantage of the present invention is its flexibility, that is, a patch is provided that easily conforms to the contours of an organ or biological surface, making the manipulation of applying the patch quicker to perform. As a result, there is less overall blood loss to the patient and less time is spent in surgery.

A hemostatic patch according to the present invention in employed by applying a "wound-contacting" surface of the patch, a surface intended to contact the wound and containing hemostatic agent(s) and optionally additives, to a bleeding wound. Then, the patch is maintained in contact with the wound for a period of time sufficient for clotting to occur at the interface between the hemostatic patch and the wound and for bleeding to be substantially arrested. Preferably the patch is maintained in contact with the wound surface for a period of about 3–20 minutes, advantageously 3–10 minutes, and more advantageously, 3–5 minutes. Where EACA, thrombin, and calcium chloride all are present on/in the matrix, the time period is preferably about 5 minutes. The patch is held in place against the biological surface preferably with light pressure, preferably by means of a sterile saline soaked sponge. Alternatively, the patch may be held in place simply by applying pressure to the patch by means of a gauze or other dry sterile material. Depending on the location of the wound, a bandage, including an elasticized bandage, can be wrapped around the patch so as to provide light pressure on the wound site.

In addition to inducing hemostasis, a patch according to the present invention is useful for hermetically sealing body tissue. For example, when air leaks from a wound in the lungs, a patch is applied to the surface surrounding the wound, held in place with light pressure for a period of time adequate to induce hemostasis, as discussed above. During that time, in addition to hemostasis, a hermetic seal forms.

Prior to applying the patch, it is preferable to soak the patch in sterile saline solution. Such a step is not required, however. Use of a hemostatic patch according to the invention, without first soaking in saline solution permits quick and simple application of the patch in field situations, such as may be encountered by an emergency medical technician or a military healthcare worker.

In one embodiment, the patch is contained within a sealed sterile package which facilitates removal of the patch without contamination. Such a package for example, can be an aluminum foil pouch or other conventional material that is easily sterilized. Radiation, advantageously gamma radiation, is applied to sterilize the patch and packaging material together.

In another embodiment, a container having dual compartments is provided. A first compartment contains distilled water, sterile saline or a sterile buffer, while the second compartment contains a patch according to the invention. In field use, the patch of the second compartment can be readily dipped into an opened first compartment and subsequently applied to the wound.

A preferred use of a patch according to the present invention is to inhibit or completely stop bleeding of a parenchymal organ, such as the liver, kidney, spleen, pancreas or lungs. Additional uses for such a patch include curbing bleeding of tissues during types of surgery such as, but not limited to, internal/abdominal, vascular (particularly for anastomosis), urological, gynecological (particularly for an episiotomy), thyroidal, neurological, ENT, tissue transplant uses, and dental surgeries.

Another use of a hemostatic patch includes topical treatment, such as for burn or tissue transplants. A patch intended for topical use according to the invention preferably contains additives, such as anti-infection medicaments. Bactericides, fungicides and wound healing agents can be added, as well. Neomycin and bacitracin are examples of certain additives that are incorporated into a patch intended for topical use, in addition to the antibacterial properties of EACA discussed above.

A hemostatic patch of the invention also is useful for treating animals, preferably humans or other mammals. Thus, both companion, livestock and wild animals can be treated with a hemostatic patch.

A patch in size and shape according to the intended use. Moreover, a standard size rectangular patch, 9.5×4.8 cm, having an uncompressed thickness of about 4–10 mm, or a compressed thickness of about 2–10 mm, advantageously 2–5 mm, may be cut to size with a pair of scissors.

One example of an advantageous matrix to which EACA and hemostatic agents and or other additives according to the invention are applied includes gelatin foam, preferably provided in a compressed form. More preferably, a Gel-Foam® matrix that is compressed to at least one-half its original thickness.

Also, a patch may be spherically, conically, cuboidally or cylindrically-shaped or prefabricated into small squares, such as for packing into a body cavity. Such an embodiment is useful for example, for a dental cavity resulting from tooth extraction. Additionally, the patch can be configured into a tampon, for example, for epistaxis (profusely bleeding nostril) or other void.

A patch intended for topical applications additionally can be applied with an adhesive tape, as a band-aid form, where the patch is adhered to an adhesive backing. Preferably the adhesive used to secure the patch is porous in areas which contact the skin.

One or more additional layers of wound dressing material, preferably a layer which aids in absorption of blood or other exudants, can be applied to a patch. Such an additional layer can be made as an integral part of the patch, thereby creating a thicker patch. Alternatively, the layer may be applied as a supplement to the backside (non-wound contacting surface) of a patch according to the invention. Particularly for topical use, the layer(s) can contain superabsorbents to wick exudant solution from the wound site. It is advised that for patches intended for internal-surgical applications, where an added layer(s) is integral with the patch, the layer(s) should be both biodegradable and pharmaceutically acceptable.

The patch can be designed to facilitate its application to anastomose or fuse ends of a blood vessel or other body lumen having been severed surgically or otherwise. To apply a patch for anastomosis, a rectangular GETR patch, for example, is wrapped around the external surface of the ends of a Dacron® graft. When the graft is positioned into place, the patch accelerates fibrin growth into the graft to seal the graft in place (hemostatically and hermetically).

A kit is provided that contains a graft and a patch according to the present invention that is designed for fitting with the ends of the graft. Alternatively, a kit is provided having a patch of the present invention pre-fitted onto at least one end of a graft.

Preferably, a wound-contacting surface of the patch is coated with a color indicator to assist the user, such as yellow vitamin $B_2$ (riboflavin) or a suitable dye, for example, hemin. By color coding the patch, the user knowingly avoids touching or otherwise contaminating the wound-contacting surface of the patch.

A patch according to the invention is made by applying to a matrix, an amount of EACA effective for inhibiting fibrinolysis in the local environment of the matrix. Advantageously, about 10–100 mg/cm$^2$ of EACA is applied to a wound-contacting surface of the matrix, more advantageously 60–70 mg/cm$^2$.

EACA, as well as the other hemostatic agents or additives described as components of a patch according to the invention, can be applied to the matrix by any of several methods which all would be performed most advantageously under sterile conditions. It is understood that conventional methods of applying the hemostatic agents and additives to a matrix comprising EACA besides those described herein can be performed as well.

Advantageously, EACA is applied as a layer to a particular surface or side of the matrix, which surface is then designated as the wound-contacting surface. This can be accomplished by spraying EACA in powder form onto the patch. Alternatively, a solution of EACA can be coated onto a matrix and dried by lyophilization or by conventional means. In another method of applying EACA, a matrix is dipped completely or partially into a sterile solution of EACA such that a sufficient amount of EACA accumulates within the matrix effective to inhibit fibrinolysis in a mammal, such that similar effectiveness to the Hemarrest patch is demonstrated.

After application of EACA to a matrix, the matrix/EACA is coated with a protein layer that facilitates EACA's adherence to the matrix. Advantageously, this protein is thrombin, although other proteinaceous or gelatin compound which facilitates such adherence could be utilized, as well. In a more advantageous embodiment, the matrix is coated with a protein layer prior to application of EACA. In a further advantageous embodiment, the matrix is treated before and after addition of EACA with a protein, preferably which is in solution with an ion additive, such as calcium (i.e., calcium chloride solution).

For example, embodiments such as GT(Ca++)E or CT(Ca++)E, are made by applying to a wound contacting surface of a matrix of gelatin foam or collagen, a first solution of thrombin dissolved in calcium chloride, the thrombin present at an amount, for example, between 1–1000 IU/cm$^2$, advantageously 1–100 IU/cm$^2$, and more advantageously 1–4 IU/cm$^2$, or 1.25 IU/cm$^2$. The thrombin is dissolved in 20–60 mM calcium chloride, preferably about 40 mM, such that an amount between 25–150 micrograms/cm$^2$, preferably 50–100 micrograms/cm$^2$, is deposited onto that surface. The next step comprises applying to the thrombin-coated matrix surface, 10–100 mg/cm$^2$ of epsilon aminocaproic acid, preferably 60–70 mg/cm$^2$, and preferably in a powder form; then, applying a second solution of thrombin in calcium chloride, which, for example contains the amounts of thrombin and calcium as described in the first solution; and then drying the thrombin, calcium chloride and epsilon aminocaproic acid on the patch. The amount of thrombin applied in the first and second solutions can vary, or, a single thrombin solution sealing step can be applied after addition of EACA. Preferably, the total amount of thrombin applied to the wound-contacting surface of the patch by the two steps is 2–10 IU/cm$^2$.

The drying step is accomplished by lyophilization, preferably. Other drying procedures appropriate for a material containing an active protein ingredient can also be employed, so long as the drying treatment does not denature the proteins or render them inactive when exposed to animal blood. Alternatively, the patch is conventionally dried, by maintaining it at room temperature for a period of 1–3 hours, followed by refrigeration overnight.

In yet another embodiment, an agent added to a matrix, in addition to EACA, thrombin, calcium chloride, includes an amount of protamine sulfate effective to neutralize heparin in the local environment of the patch. Protamine sulfate is added in an amount between 1–15 mg/cm$^2$ of said matrix, preferably in an amount between 2–5 mg/cm$^2$ of a wound contacting surface of the matrix.

Likewise, RGD or RGDS peptide can be dissolved in double distilled water and sprayed onto a wound-contacting surface of the patch. A patch advantageously contains an amount of RGD effective to enhance clot formation. RGD or RGDS is applied to a patch advantageously in an amount between 110–130 mg/cm$^2$. Thus, a standard size patch would contain about 1–10 mg/patch or about 5–7 mg/patch of RGD or RGDS.

It should be noted that, like EACA, the hemostatic agents or additives described in the foregoing paragraphs can be applied to a matrix as a layer, for example, by spraying them onto the wound-contacting surface of the matrix in dried forms. Alternatively, a matrix can be dipped or coated with a solution containing the hemostatic agent/additive. It is desirable that the matrix and agents commingle, particularly when the patch is exposed to a body fluid such as blood, which permits the dried agents to solubilize and mix. Thus, a patch can be provided wherein the hemostatic agent or mixture of hemostatic agents are absorbed into the pores or interstices of the matrix, or, the agents can be layered on a surface of the matrix and upon solubilizing the agents by addition of body fluid, the desired commingling is achieved.

The matrix can be coated with appropriate hemostatic agents described in the above embodiments on one or all surfaces. In a preferred embodiment, the hemostatic agents and additives are coated on only one surface (the wound-contacting surface). Such an arrangement avoids inducing hemostasis between the wound and a non-wounded tissue in the vicinity of the patch. In an embodiment intended for packing a void in body tissue, for example, the patch is coated with hemostatic agent(s)/additive(s) on all surfaces.

A kit according to the invention comprises any of the above described hemostatic patch embodiments (which vary in ways including hemostatic agent(s) and additive(s) utilized, shape or size) according to the invention and a package, wherein the patch is contained within a sealed sterile package which facilitates removal of the patch without contamination. The kit can contain multiple patches, preferably wherein each patch is contained within a separate sealed sterile package. A kit designed for field/military use can, in addition to a hemostatic patch, further include disposable pre-sterilized surgical instruments, such as a scalpel, clamp, tourniquet, elastic or inelastic bandage, or the like.

Another type of kit comprises a patch containing agents added to the matrix including thrombin, EACA calcium chloride, and protamine sulfate. Such a kit can be prescribed, for example, to patients requiring anticoagulant therapy, to avert the risk of serious bleeding which can occur from a minor injury. The availability of such a patch can reduce postoperative hospitalization for patients on dicumarol who underwent surgery.

The present invention is further described with reference to the following, illustrative examples. Unless defined otherwise, all technical and scientific terms used herein have the same meaning as commonly understood by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well known to one of ordinary skill in the art. The materials, methods and examples are illustrative only and not limiting.

EXAMPLE 1

THE EFFECTS OF EACA ON THROMBIN ACTIVATION

A two-part experiment was designed to test whether thrombin activation in the presence of EACA (A) is accelerated and (B) is pH dependent.

A. Effect of Time Incubated at 37° C.

The first part of this study examined activation of thrombin and its degradation in H$_2$O after incubation at 37° C. The assay used was a colorimetric cleaving of a tripeptide, TFA-phe-pro-arg-AFC, where the AFC is the colorometric tag. Seventeen mg of this substrate was dissolved in 200 µl DMSO. Thrombin was made up as 10 units/ml. The "TEST" solution contained 100 µl substrate and 200 µl of the thrombin solution; a blank contained the same amount of substrate and 200 µl of H$_2$O.

FIG. 1 labeled as "ACTIVATION OF THROMBIN SOLUTION AT 37° C." shows the results of that experiment. The optical density in all of these experiments is an indication of the color and therefore the amount of cleavage of the enzyme that has taken place.

The slope of the black-box line indicates that thrombin activation of thrombin dissolved in H$_2$O takes place slowly over a 172 minute time period. The blank, containing substrate and H$_2$O, shows no change in optical density, indicating that no activation, or cleaving of the peptide has occurred.

B. Thrombin Activation by EACA: A pH Effect

In this experiment, the hypothesis that the activation of thrombin by EACA was due to EACA's effect of increasing pH was tested.

All solutions were prepared at the same concentration as indicated in part A above, except EACA which was made up at a concentration of 50 mg/ml. The following samples were prepared:

1. 50 µl Thrombin+925 µl H$_2$O+25 µl substrate
2. 50 µl Thrombin+925 µl Tris buffer@pH 7.02+25 µl substrate
3. 50 µl Thrombin+925 µl Tris buffer@pH 7.62+25 µl substrate
4. 50 µl Thrombin+925 µl Tris buffer@pH 7.80+25 µl substrate
5. 50 µl Thrombin+925 µl Tris buffer@pH 8.01+25 µl substrate
6. 50 µl Thrombin+425 µl EACA sol.+500 µl H$_2$O+25 µl substrate
7. 50 µl Thrombin+425 µl EACA sol.+500 µl Tris buffer@pH 7.02+25 µl substrate
8. 50 µl Thrombin+425 µl EACA sol.+500 µl Tris buffer@pH 7.62+25 µl substrate
9. 50 µl Thrombin+425 µl EACA sol.+500 µl Tris buffer@Ph 7.80+25 µl substrate
10. 50 µl Thrombin+425 µl EACA sol.+500 µl Tris buffer@Ph 8.01+25 µl substrate Each tube was placed in a 37° C. waterbath and removed periodically to be read each 5' for a total of 60'. Results are summarized in FIG. 2. In the legend, samples 1–10 listed vertically in the legend correspond to samples 1–10 immediately above, while "T" represents thrombin.

The results indicate clearly that the action of EACA is a pH effect and that Tris buffer-adjusted solutions had a similar effect as the pH was increased. In all cases, the plateau may not be accurate since the saturation of the instrument occurs near to the maximum optical density recorded.

At 37° C., the results indicated clearly that the action of EACA is a pH effect. Calcium ion appears to enhance this pH-mediated activation.

EXAMPLE 2

EACA EXERTS AN ANTIBACTERIAL EFFECT

EACA was shown to inhibit both *Staph. aureus* and *E. coli* in a dose-dependent manner by the following method.

Culture plates and EACA discs were prepared as follows: Whatman filter paper discs of 5.4 cm in diameter and 22.9 cm$^2$ in area were placed in beakers of almost the same diameter. EACA (229 mg) was dissolved in 250 µl of double distilled H$_2$O and used to make the final concentrations. All concentrations of EACA were applied in 250 µl of H$_2$O. Concentrations of 0, 10, 20, 30, 40, 50, 60, 70, 80, 90 and 100 mg/cm$^2$ were prepared. After application of EACA solutions, the discs were allowed to dry and frozen to ensure stability.

Discs for application to agar plates were made with a paper punch, at a size of about 6.35 mm. Agar plates were poured in two increments.

A first increment of 1.5% Brain-Heart Infusion agar was prepared and autoclaved. After cooling to approximately 55° C., 12 mls were added to each 100 mm×15 mm petri dish. Plates were allowed to cool to room temperature, wrapped in parafilm and refrigerated. Brain-Heart Infusion broth was prepared and autoclaved. When the temperature was cooled to room temperature, a 1 ml aliquot of *Staph. aureus* or *E. coli* was added and the broth incubated overnight at 37° C.

Figure 3A:
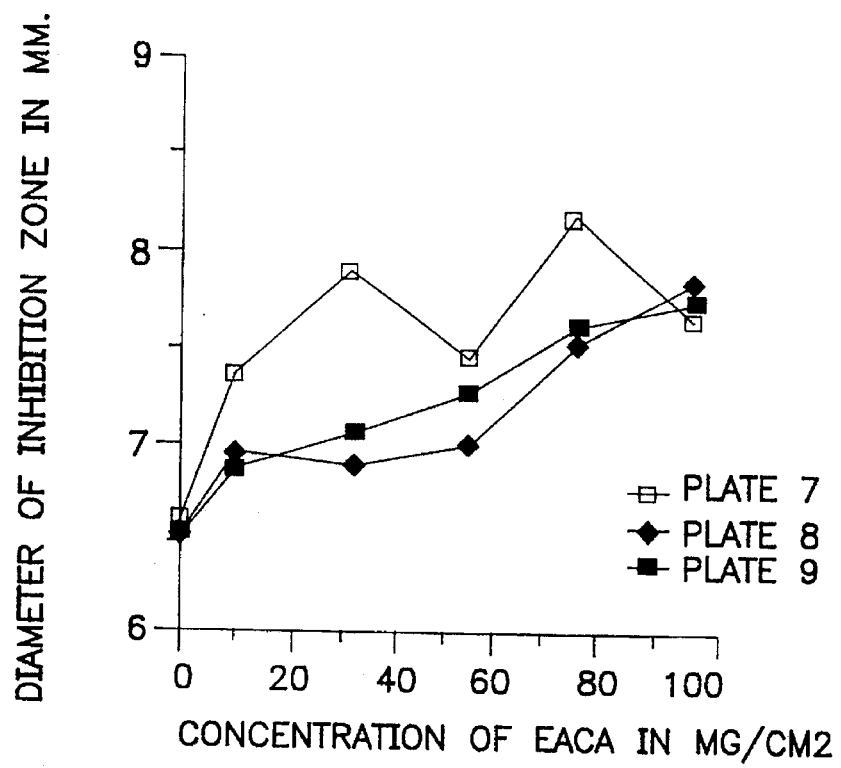
FIG. 3A and FIG. 3B each show inhibition by EACA of *Staph. aureus* growth in the presence of various concentrations of EACA.
Figure 3B:
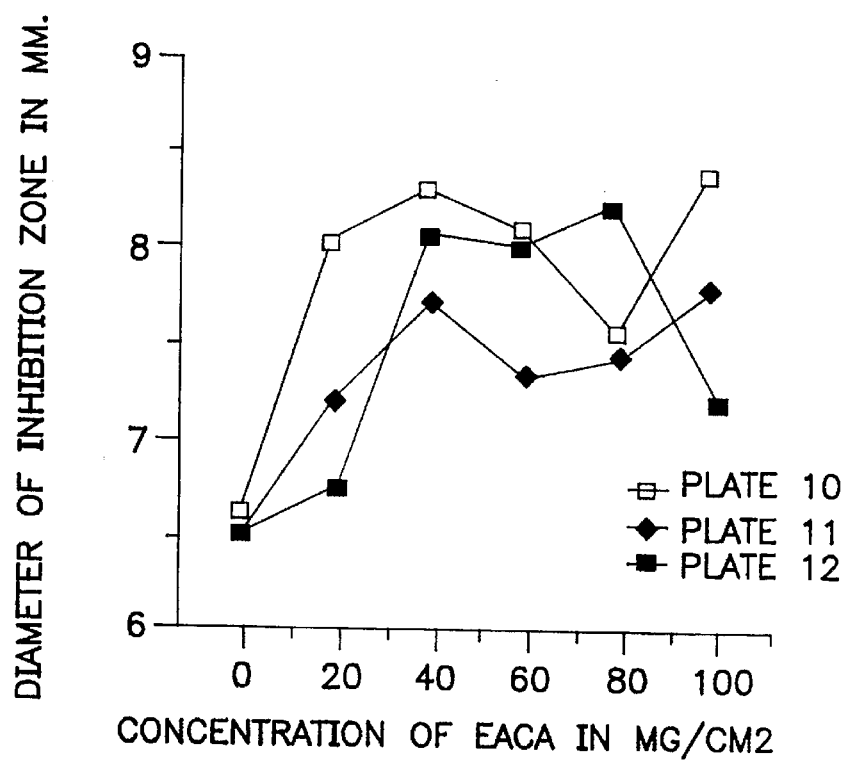
Figure 4A:
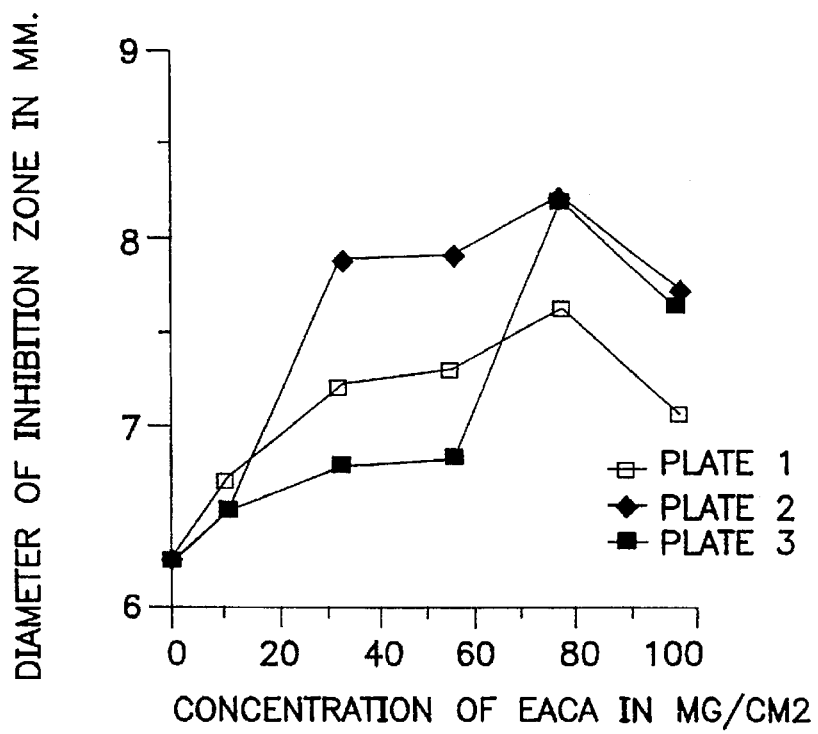
FIG. 4A and FIG. 4B each show inhibition by EACA of *E. coli* growth in the presence of various concentrations of EACA.
Figure 4B:
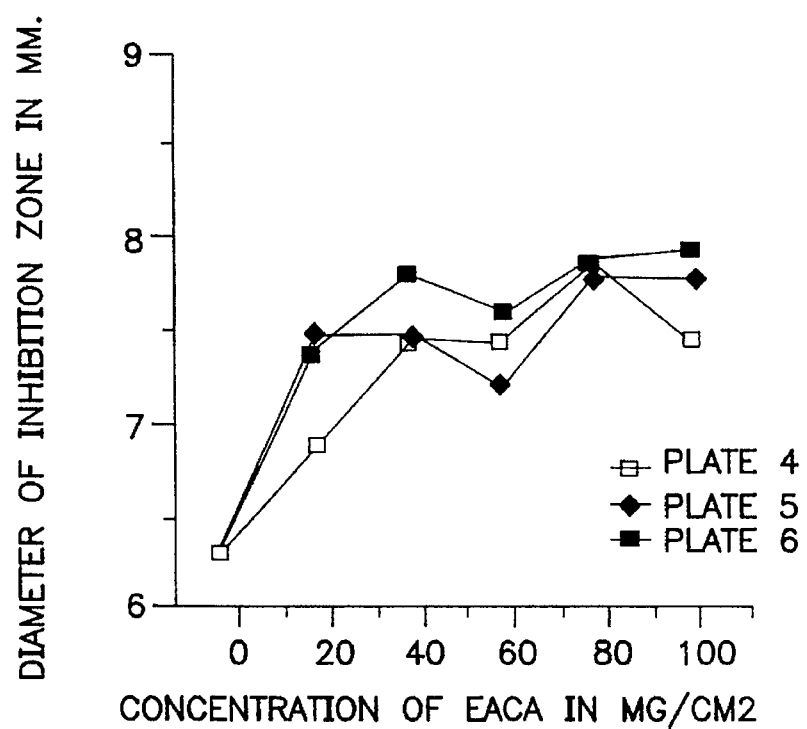

The following day, a second increment of 1.2% Brain-Heart Infusion agar was prepared and when cooled to 48° C. after autoclaving, 2 ml of each culture was added to separate flasks of agar and 1 ml of these mixtures was added to each culture plate. This top layer was allowed to harden at room temperature. Two sets of five discs containing EACA at varying concentrations were added to each plate, in addition to a control disc containing zero mg/cm$^2$ EACA. The complete results are listed in Table 2. FIG. 3A and FIG. 3B each show inhibition by EACA of *Staph. aureus* growth graphically, for each set of various concentrations of EACA, while FIG. 4A and FIG. 4B each show inhibition by EACA of *E. coli* growth for each set of varying concentrations of EACA.

Results of observation and measurement of the zone inhibition reveal that in almost all instances, there is an incremental change in this zone of inhibition related to the concentration of EACA. The exceptions are that the 60 mg/cm$^2$ did not follow the trend, but was equal to or decreased in relation to the 40 mg/cm$^2$. The 90 and 100 mg/cm$^2$ zones were not always increases. The consistency of these variations appear to be related to the disc preparation rather than a biological variation.

TABLE 2

Results: Inhibition of *E. coli* (Plates 1–6) and *Staph. aureus* (Plates 7–12) Growth by EACA

| Date | Plate Number | Organism | Conc. of EACA in mg/cm2 | DIAMETER OF INHIBITION | % > CONTROL | % OF MAXIMUM |
|---|---|---|---|---|---|---|
| 10/22/93 | 1 | E. coli | control | 6.35 | 0.00 | 77.00 |
|  |  |  | 10 | 6.95 | 9.40 | 84.20 |
|  |  |  | 30 | 7.65 | 20.50 | 92.70 |
|  |  |  | 50 | 7.75 | 22.00 | 93.90 |
|  |  |  | 70 | 8.25 | 29.90 | 100.00 |
|  |  |  | 90 | 7.50 | 18.10 | 90.90 |
| 10/22/93 | 2 | E. coli | control | 6.35 | 0.00 | 70.20 |
|  |  |  | 10 | 6.70 | 5.50 | 74.00 |
|  |  |  | 30 | 8.55 | 34.60 | 94.50 |
|  |  |  | 50 | 8.60 | 35.40 | 95.00 |
|  |  |  | 70 | 9.05 | 42.50 | 100.00 |
|  |  |  | 90 | 8.35 | 31.50 | 92.30 |
| 10/22/93 | 3 | E. coli | control | 6.35 | 0.00 | 70.60 |
|  |  |  | 10 | 6.70 | 5.50 | 74.40 |
|  |  |  | 30 | 7.05 | 11.00 | 78.30 |
|  |  |  | 50 | 7.10 | 11.80 | 78.80 |
|  |  |  | 70 | 9.00 | 41.70 | 100.00 |
|  |  |  | 90 | 8.25 | 29.90 | 91.70 |
| 10/22/93 | 4 | E. coli | control | 6.35 | 0.00 | 77.40 |
|  |  |  | 20 | 7.05 | 11.00 | 86.00 |
|  |  |  | 40 | 7.70 | 21.30 | 93.90 |
|  |  |  | 60 | 7.70 | 21.30 | 93.90 |
|  |  |  | 80 | 8.20 | 29.10 | 100.00 |
|  |  |  | 100 | 7.75 | 22.00 | 94.50 |
| 10/22/93 | 5 | E. coli | control | 6.35 | 0.00 | 78.40 |
|  |  |  | 20 | 7.70 | 21.30 | 95.10 |
|  |  |  | 40 | 7.75 | 22.00 | 95.70 |
|  |  |  | 60 | 7.45 | 17.30 | 92.00 |
|  |  |  | 80 | 8.10 | 27.60 | 100.00 |
|  |  |  | 100 | 8.10 | 27.60 | 100.00 |
| 10/22/93 | 6 | E. coli | control | 6.35 | 0.00 | 76.50 |
|  |  |  | 20 | 7.60 | 19.70 | 91.60 |
|  |  |  | 40 | 8.10 | 27.60 | 97.60 |
|  |  |  | 60 | 7.90 | 24.40 | 95.20 |
|  |  |  | 80 | 8.25 | 29.90 | 99.40 |
|  |  |  | 100 | 8.30 | 30.70 | 100.00 |

TABLE 2-continued

Results: Inhibition of *E. coli* (Plates 1–6) and *Staph. aureus* (Plates 7–12) Growth by EACA

| Date | Plate Number | Organism | Conc. of EACA in mg/cm2 | DI- AM- ETER OF IN- HIB- ITION | % > CON- TROL | % OF MAX- I MUM |
|---|---|---|---|---|---|---|
| 10/22/93 | 7 | S. aureus | control | 6.60 | 0.00 | 77.20 |
| | | | 10 | 7.55 | 14.40 | 88.30 |
| | | | 30 | 8.20 | 24.20 | 95.90 |
| | | | 50 | 7.65 | 15.90 | 89.50 |
| | | | 70 | 8.55 | 29.50 | 100.00 |
| | | | 90 | 7.90 | 19.70 | 92.40 |
| 10/22/93 | 8 | S. aureus | control | 6.55 | 0.00 | 80.90 |
| | | | 10 | 7.10 | 8.40 | 87.70 |
| | | | 30 | 7.00 | 6.90 | 86.40 |
| | | | 50 | 7.15 | 9.20 | 88.30 |
| | | | 70 | 7.75 | 18.30 | 95.70 |
| | | | 90 | 8.10 | 23.70 | 100.00 |
| 10/22/93 | 9 | S. aureus | control | 6.55 | 0.00 | 81.90 |
| | | | 10 | 7.00 | 6.90 | 87.50 |
| | | | 30 | 7.20 | 9.90 | 90.00 |
| | | | 50 | 7.45 | 13.70 | 93.10 |
| | | | 70 | 7.85 | 19.80 | 98.10 |
| | | | 90 | 8.00 | 22.10 | 100.00 |
| 10/22/93 | 10 | S. aureus | control | 6.60 | 0.00 | 79.00 |
| | | | 20 | 8.05 | 21.90 | 96.40 |
| | | | 40 | 8.30 | 25.80 | 99.40 |
| | | | 60 | 8.10 | 22.70 | 97.00 |
| | | | 80 | 7.55 | 14.40 | 90.40 |
| | | | 100 | 8.35 | 26.50 | 100.00 |
| 10/22/93 | 11 | S. aureus | control | 6.50 | 0.00 | 83.90 |
| | | | 20 | 7.20 | 10.80 | 92.90 |
| | | | 40 | 7.70 | 18.50 | 99.40 |
| | | | 60 | 7.30 | 12.30 | 94.20 |
| | | | 80 | 7.40 | 13.80 | 95.50 |
| | | | 100 | 7.75 | 19.20 | 100.00 |
| 10/22/93 | 12 | S. aureus | control | 6.50 | 0.00 | 79.30 |
| | | | 20 | 6.75 | 3.80 | 82.30 |
| | | | 40 | 8.05 | 23.80 | 98.20 |
| | | | 60 | 8.00 | 23.10 | 97.60 |
| | | | 80 | 8.20 | 26.20 | 100.00 |
| | | | 100 | 7.20 | 10.80 | 87.80 |

EXAMPLE 3

A COMPARISON BETWEEN G(Ca++)TE AND TACHOCOMB®

A. Experimental Conditions

1. Patch Preparation

An absorbable gelatin sponge, namely a gelatin foam matrix (GelFoam®, UpJohn Co.) was obtained. *Physician's Desk Reference* 2451, 47th Edition Dowd (ed.), Medical Economics Data (1993). Thereafter, 1.25 IU/cm$^2$ bovine thrombin was applied to a surface of the gelatin foam. Next, either 10 mg/cm$^2$ or 100 mg/cm$^2$ of EACA was applied to that same surface, followed by an application of another 1.25 IU/cm$^2$ application of bovine thrombin. The patches were allowed to dry and left in a refrigerator overnight. A "blank" gelatin foam patch, which was not treated with thrombin or EACA was also tested in the kidney.

TachoComb® patches were obtained and applied according to the manufacturer's instructions. That is, prior to preparation, the TachoComb® patches were dipped in sterile saline and applied to bleeding organs with light pressure for five minutes.

2. Organ Preparation

A lobe of pig liver was surgically isolated and three lesions approximately 1×5 cm in size were created. Blood flowed freely from each of the lesions. Each of the patches discussed in part A. (above), were applied and kept under pressure by a saline soaked sponge for five minutes and the pressure was released. Patches were evaluated by their ability to control hemorrhage in terms of (a) leakage, (b) ability to withstand increased vascular pressure, (c) the resistance offered when attempting to peel the patch from the lesion, and (d) events of clot formation in the lesion.

For the liver, pressure tests were performed by raising the arterial pressure by injecting 0.2 ml 1/1000 epinephrine.

For renal studies, both poles (ends) of the kidney were surgically removed to a depth of approximately 0.5 cm, while the renal artery was clamped. The clamp was removed after the test patches were placed and pressure applied with a saline soaked surgical sponge for five minutes.

B. Summary of Results

In liver, when the pressure was removed and after five minutes, both patches according to the invention showed good control of hemorrhage, with only a little bleeding from the edge in the 100 mg patch and no bleeding from the 10 mg patch. After 9–13 minutes, the TachoComb® patch was the only patch leaking or bleeding from the edge.

A small amount of blood was present on the surface of the 100 mg patch, while none was present on the 10 mg patch.

When the patches were removed from the same liver free blood was present coming from the 100 mg and TachoComb® lesions. A greater flow was observed coming from the TachoComb® patch. Much of the clot from the TachoComb® site stayed with the patch when it was peeled back. A piece of the gelatin foam patch was incorporated into the 10 mg site.

When epinephrine was injected, the TachoComb® patch still dripped blood from the edges after 18 minutes. The peel test after 20 minutes showed the TachoComb® patch with minimal adhesion, the clot stuck to the patch, and the wound continued to bleed. In the lesion with the 100 mg patch, blood also flowed, but not as much as the TachoComb® patch. The 10 mg patch had the least bleeding of any of the patches and had both good incorporation of the patch into the lesion and good clot formation, with some minimal adhesion to the periphery.

In the kidney, there was not much difference between the TachoComb® and the 100 mg patch lesions. There was no bleeding before or after epinephrine injections. When the patches were peeled at 20 minutes, the TachoComb® patch had very good adhesive qualities, good clot formation, but some free blood. The 100 mg patch did not have as good adhesiveness, but had a well-formed clot and no hemorrhage. When a blank gelatin patch and 10 mg patches according to the invention were compared, the 10 mg patch definitely was better. Five minutes after the pressure release, there was free blood under the 100 mg patch while there was some bleeding around the edge of the 10 mg patch. This was unchanged after epinephrine, but when an experimental peel test was done by removing the patch and observing clot formation, the clot was not as well-formed under the blank patch. Further, free blood was present, and there was a blot stain dark with blood on the dry surgical sponge held against the patch to detect blood or serum penetrating the patch. There was good adhesion of the 100 mg patch to the surface even when the patch is removed. The 10 mg patch had fair adhesion around the edges and some free blood. When the patch was lifted there was evidence of good clot formation and no bleeding, thereby providing a light pink blot test measured by the dry surgical sponge held against the patch.

When a patch containing 2.5 IU/cm$^2$ thrombin and 100 mg/cm$^2$ epsilon aminocaproic acid was applied to a kidney lesion a light pink color was seen which indicated that virtually no free blood penetrated through the patch. No blood was present on the sponge that held the hemostatic patch against the organ.

A lesion on the opposite pole of the same kidney was covered with a TachoComb® patch. The latter patch was darker, which indicates that more blood was coming through the patch matrix. The lower edges of that patch were looser as compared to the Hemarrest™ patch. Fresh blood could be seen on a dry sponge held against the organ for the purpose of aiding in detection of fresh blood.

EXAMPLE 4

HEMOSTATIC EFFICACY ACHIEVED BY THE GE(Ca++) PATCH

1) Pig splenic lesions were created as discussed in Example 3. As seen in FIG. 10, no leakage was observed from the GE(Ca++) patch, while some was observed from the GT(Ca++)E patch. In 10 minutes, there was slight leakage from the centers of both, which was stopped by 15 minutes. When the patches were removed, there was no difference in a test blotting performed on the surface of the patch, as both test blots were light pink. Very good adhesion was observed for both patches, as well as large, well-formed clots. In the GE(Ca++) patch, the clot adhered to the patch but not the lesion.

2) In the liver, neither showed bleeding at any observation. When peeled, the patches both had good adhesion, but the GE(Ca++) patch bled freely after the patch was removed. In contrast, the GT(Ca++)E patch had some incorporation and a good clot. The GE(Ca++) did not seem to have a good clot.

3) The kidneys had unexpected findings. The GE(Ca++) patch had no evident leakage while the GT(Ca++)E leaked steadily. At 10 minutes, the leakage had lessened in the GT(Ca++)E patch, and at 15 minutes, there was no further leakage in either. When the patches were removed, both had good adhesion, some incorporation of the GT(Ca++)E patch, but both bled in the absence of the patch.

The conclusion from this one experiment suggests that there is little difference between the treatments although clot formation appears to be better with the addition of thrombin. This means that a first-aid bandage that is stable under more severe exposure to heat may be effective without the presence of thrombin.

EXAMPLE 5

THE ("RGD") PATCH

The study has both parts I and II. Part 1: Patches CTR, CTE(f), GT(f)E(f) and a plain gelfoam (G) patch were applied to lesions made on the spleen of an anesthetized pig. The symbol "(f)" denotes the compound immediately preceding it as a freshly-applied compound. That is, E(f) denotes EACA that is freshly applied to a patch very soon (less than about three hours) after it is made.

1) Leakage: When the sponge pressure was removed from the patches, the G patch had virtually no leakage. This was true of the CTE(f)R patch as well, but the CTR patch showed much bleeding. Shortly thereafter, the results were recorded as similar.

2) Peel/Adhesion: All three patches stuck to the saline-soaked sponges and removal of sponge pressure was done carefully to prevent their removal from the lesion; thus adhesion in all patches was minimal at that time. Patch G did show some adhesion, but CTR and CTE(f)R showed good adhesion even though they each had some clot formation, best in CTE(f)R. Approximately 6 minutes after removing the pressure, the gelatin foam showed very good adhesiveness and poor clot formation. Neither of the other patches showed good adhesion qualities, while the CTR some clot and CTE(f)R had a large, excellent clot.

Part II: More lesions were created on the spleen and all results were compared. Patches applied were CTE(f) and GT(f)E(f).

1) Leakage: Neither the CTE nor the GT(f)E(f) patch showed leakage at removal of sponge pressure. Five minutes later, the vein was occluded and intravascular pressure increased and lesions made in both parts were evaluated. The time for the increased pressure test performed after the sponge was released in Part I is 27 minutes and in Part II, only 5 minutes. The gelatin foam only patch (G) was not leaking at all; neither were CTR, ** CTE(f)R. In comparing the two patches with T and EACA using either the gelatin foam or collagen matrix, the gelatin foam patch, GT(f)E(f), showed less leakage than the collagen based patch, CTE. In fact, the CTE patch leaked more as the venous pressure was raised.

2) Peel/Adhesion: Two minutes after removing the sponge pressure and when comparing CTE(f), collagen+T+EACA and GT(f)E(f), the gelatin foam based patch similarly treated showed very good adhesion to both the lesion and the surrounding tissue. The CTE patch with the collagen base had little or no adhesion. 10 minutes after removing sponge pressure (part II patches GT(f)E(f) and CTE(f)) and with the intravascular pressure still elevated, all patches from Part I and Part II were evaluated together. The time interval was about 32 minutes after initial sponge pressure removal for those patches from Part I (CTR, G, and CTE(f)R). The results were as follows: Patch CTR) No adhesion, good clot formation and little leakage. Patch G) Strong adhesion to surrounding tissue, no adhesion to lesion, much leaking. Patch CTE(f)R) No adhesion, good clot formation, little leakage. Patch GT(f)E(f)) Good adhesion to lesion, good clot formation, little leakage. Patch CTE(f) No adhesion, good clot formation, little leakage.

3) A further assessment of splenic lesions was made (Part I) 58 minutes after initial sponge pressure release, Part II, −36 minutes after initial pressure release. The patches were removed at this time. The results of this assessment are: Patch TR) Moderate clot formation, little, if any, leakage. Patch G) Leakage, but remainder of gelatin foam stuck to lesion. Patch CTE(f)R) Excellent clot, no leakage. Patch GT(f)E(f)) Good clot formation, little, if any, leakage. Patch CTE(f) good clot formation, virtually dry.

4) A final assessment of these splenic lesions was made 37 minutes later. Patch CTR) Dry to the blot test (placing a dry surgical sponge on the lesion), clot is developed, no collagen incorporated into lesion. Patch G) Dry to the blot test, gelatin foam incorporated into the lesion. Patch CTE(f)R) Absolutely no blood elements on sponge after blotting; clot is excellent, filling lesion and extending onto the surrounding normal area. Patch GT(f)E(f)) Serum staining on sponge, but good clot and gelatin sponge incorporated into the lesion. Patch CTE(f) Dry to blot test; similar to CTE(f)R.

We claim:

1. A hemostatic patch suitable for rapidly and without pre-moistening arresting bleeding from a lesion on a parenchymal organ, in the form of a dry sterile storage stable fibrogen-free flexible sheet of a biodegradable matrix selected from the group consisting of absorbable gelatin, calcium alginate, calcium/sodium alginate, collagen and oxidized regenerated cellulose and containing a hemostatic agent on one face only thereof, which hemostatic agent comprises an amount of thrombin effective to promote accelerated hemostasis and an amount of epsilon aminocaproic acid effective to inhibit fibrinolysis and to accelerate the activation of the thrombin when the patch is applied to the bleeding lesion.

2. A hemostatic patch according to claim 1, wherein the biodegradable matrix is a foam.

3. A hemostatic patch according to claim 1, wherein the biodegradable matrix is absorbable gelatin.

4. A hemostatic patch according to claim 1, wherein the patch contains one or more of a source of calcium ions, RGD peptide, RGDS peptide, protamine sulfate and buffer.

5. A hemostatic patch according to claim 1, wherein the thrombin is bovine thrombin.

6. A hemostatic patch according to claim 1, wherein the epsilon aminocaproic acid is present in an amount from about 10–100 mg/cm$^2$ of the wound-contacting surface of the matrix.

7. A hemostatic patch according to claim 1, wherein the thrombin is present in an amount between 1–4 IU/cm$^2$ of the wound-contacting surface of the matrix.

8. A hemostatic patch according to claim 1, wherein calcium ions are present in an amount equivalent to between 25–150 micrograms CaCl$_2$/cm$^2$ of the wound-contacting surface of the matrix.

9. A hemostatic patch according to claim 1, wherein the biodegradable matrix is an absorbable gelatin foam; wherein the patch optionally contains one or more of RGD peptide, RGDS peptide, protamine sulfate and buffer; wherein the epsilon aminocaproic acid is present in an amount between 60–70 mg/cm$^2$ of the wound-contacting surface of the matrix; wherein the thrombin is present in an amount between 1–4 IU/cm$^2$ of the wound-contacting surface of the matrix; and wherein calcium ions are present in an amount equivalent to between 25–150 micrograms of CaCl$_2$/cm$^2$ of the wound-contacting surface of the matrix.

10. A sterile package containing a hemostatic patch according to claim 1.

11. A sterile package containing a hemostatic patch according to claim 9.

12. A method for stanching bleeding from a wound, which comprises applying to the wounded surface a hemostatic patch according to claim 1.

13. A method for stanching bleeding from a wound, which comprises applying to the wounded surface a hemostatic patch according to claim 9.

14. A method for effecting hemostasis in a bleeding parenchymal organ, which comprises applying to the bleeding surface of the parenchymal organ a hemostatic patch according to claim 1.

15. A method for effecting hemostasis in a bleeding parenchymal organ, which comprises covering the bleeding surface of the parenchymal organ with a hemostatic patch according to claim 9.

16. A method according to claim 15, which comprises manually pressing the hemostatic agent-containing surface of the patch against the wounded surface of the parenchymal organ for a period of time until clotting has occurred at the interface between the hemostatic patch and the wounded surface.

17. A method according to claim 15, wherein the parenchymal organ is a liver, kidney or spleen.

* * * * *